United States Patent [19]

Crounse et al.

[11] 4,209,618

[45] Jun. 24, 1980

[54] MORPHOLINODIPHENYLPHTHALIDES

[75] Inventors: Nathan N. Crounse, Cincinnati; Paul J. Schmidt, Sharonville, both of Ohio

[73] Assignee: Sterling Drug Inc., New York, N.Y.

[21] Appl. No.: 894,682

[22] Filed: Apr. 10, 1978

Related U.S. Application Data

[60] Division of Ser. No. 740,592, Nov. 10, 1976, Pat. No. 4,094,877, which is a continuation-in-part of Ser. No. 527,757, Nov. 27, 1974, Pat. No. 4,032,527, which is a continuation-in-part of Ser. No. 314,443, Dec. 12, 1972, Pat. No. 4,096,176.

[51] Int. Cl.² .......................................... C07D 413/10
[52] U.S. Cl. ............................................... 544/153
[58] Field of Search ........................................ 544/153

[56] References Cited

U.S. PATENT DOCUMENTS

| 3,122,551 | 2/1964 | Zaugg et al. | 544/153 |
|---|---|---|---|
| 3,944,570 | 3/1976 | Houlihan et al. | 544/153 |
| 4,094,877 | 6/1978 | Crounse et al. | 260/343.4 |

OTHER PUBLICATIONS

Kozutsumi et al. Chem. Abstracts. vol. 80, 1974, 72084e.

*Primary Examiner*—Natalie Trousof
*Assistant Examiner*—Jane T. Fan
*Attorney, Agent, or Firm*—Theodore C. Miller; B. Woodrow Wyatt

[57] ABSTRACT

Substituted 3,3-diphenylphthalides, useful as color precursors, particularly in the art of pressure-sensitive duplicating systems and heat-sensitive marking systems, are prepared by condensing substituted 2-benzoylbenzoic acids with substituted anilines.

4 Claims, No Drawings

MORPHOLINODIPHENYLPHTHALIDES

CROSS-REFERENCE TO RELATED APPLICATIONS

This application is a division of our copending application Ser. No. 740,592, filed Nov. 10, 1976 now U.S. Pat. No. 4,094,877, which is a continuation-in-part of our copending application Ser. No. 527,757, filed Nov. 27, 1974 and now U.S. Pat. No. 4,032,527, which is a continuation-in-part of our copending application Ser. No. 314,443, filed Dec. 12, 1972, now U.S. Pat. No. 4,096,176.

BACKGROUND OF THE INVENTION

1. Field of the Invention

This invention relates to substituted 3,3-diphenylphthalides useful as color precursors, substituted 2-benzoylbenzoic acids useful as intermediates in preparing them, processes for preparing them, and pressure-sensitive duplicating systems and heat-sensitive marking systems comprising them.

2. Description of the Prior Art

In the art of pressure-sensitive duplicating systems and heat-sensitive marking systems color precursors in current use are colorless under neutral or basic conditions, but become colored when contacted with an acidic material such as silica gel, a phenolic resin or an acidic clay. Two known diphenylphthalide color precursors are malachite green lactone of Formula A, which is described in Beilsteins Handbuch der Organischen Chemie (Vierte Auflage, Band XVIII, Seite 617, 1934), and crystal violet lactone of Formula B, which is described in U.S. Pat. No. 2,417,897 (Reissue 23,024).

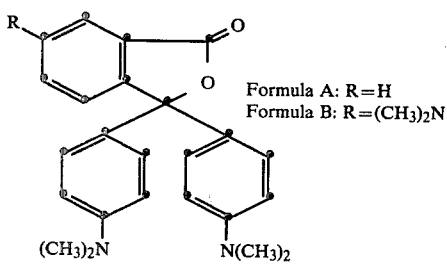

Formula A: R=H
Formula B: R=(CH$_3$)$_2$N

Two of many patents which describe pressure-sensitive duplicating systems containing malachite green lactone and crystal violet lactone are U.S. Pat. No. 2,548,364 and U.S. Pat. No. 2,548,365. In such systems malachite green lactone and crystal violet lactone, the latter of which is widely used, produce images whose colors are intense but not deep. Depth of color is desired for easier readability and better xerographic copiability of the images. In order to overcome lack of color depth, other color precursors have been mixed with crystal violet lactone as described, for example, in U.S. Pat. No. 3,525,630. An unsolved problem in the art has been both intensity and depth of color in the same molecule. The present invention is a solution to the problem.

PRIOR PUBLICATION

Japanese Application Publication No. 3467, published Jan. 31, 1972 (Chemical Abstracts, vol. 77, abstract no. 21580u, p. 122, 1972) describes in English translation a genus of diphenylphthalides of Formula C wherein $R_1$, $R_2$, $R_3$ and $R_4$ are alkyl, alkoxy penyl, β-oxyethyl or β-haloethyl, X is inter alia alkyl amino, Y is hydrogen, chlorine or bromine, and n is an integer from 1 through 4 and one species, whose structural formula is alleged to be Formula D and which is the only described species of the genus wherein X is alkyl amino (the product of Example 3).

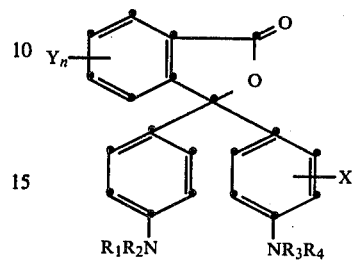

Formula C

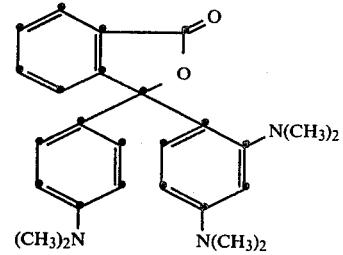

Formula D

The present invention was reduced to practice before Jan. 31, 1972, the publication date of Japanese Application Publication No. 3467. Moreover, it is believed that the product of Example 3 of Japanese Application Publication No. 3467 is not in fact the compound of Formula D, since the properties thereof do not correspond to the properties of the product of Example 1B of this application, which has Formula D.

SUMMARY OF THE INVENTION

In its substituted 3,3-diphenylphthalide aspect the invention provides 3-(2-X-4-X-phenyl)-3-(2-Y$^2$-4-Y$^4$-phenyl)-4-Z$^4$-5-Z$^5$-6-Z$^6$-7-Z$^7$-phthalide of the formula

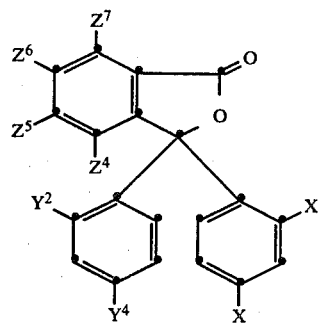

Formula I wherein:

X is dialkylamino wherein alkyl is non-tertiary alkyl of one to four carbon atoms;

Y$^2$ is hydrogen, non-tertiary alkyl of one to four carbon atoms, dialkylamino wherein alkyl is non-tertiary alkyl of one to four carbon atoms, alkanoylamino of two to five carbon atoms, non-tertiary alkoxy one to four carbon atoms or halo;

$Y^4$ is the same as $Y^2$ when $y^2$ is dialkylamino; or dialkylamino, pyrrolidino, piperidino, morpholino, alkylbenzylamino, alkyl(4-alkoxyphenyl)amino or alkyl(Q-(CH$_2$)$_n$)-amino, wherein alkyl is non-tertiary alkyl of one to four carbon atoms, alkoxy is non-tertiary alkoxy of one to four carbon atoms, Q is hydroxy or chloro and n is two to four when $Y^2$ is other than dialkylamino;

$Z^4$ is hydrogen or halo;

$Z^5$ is hydrogen or halo; or non-tertiary alkyl of one to four carbon atoms, nitro, amino or dialkylamino wherein alkyl is non-tertiary alkyl of one to four carbon atoms when $Z^4$, $Z^6$ and $Z^7$ are each hydrogen;

$Z^6$ is hydrogen or halo; or non-tertiary alkyl of one to four carbon atoms, nitro, amino or dialkylamino wherein alkyl is non-tertiary alkyl of one to four carbon atoms when $Z^4$, $Z^5$ and $Z^7$ are each hydrogen; and $Z^7$ is hydrogen or halo.

The compounds of Formula I are useful as color precursors, particularly in the art of pressure-sensitive duplicating systems and heat-sensitive marking systems.

In its substituted 2-benzoylbenzoic acid aspect the invention provides 2-(2-$Y'^2$-4-$Y'^4$-benzoyl)-3-$Z^4$-4-$Z'^5$-5-$Z'^6$-6-$Z^7$-benzoic acid of the formula

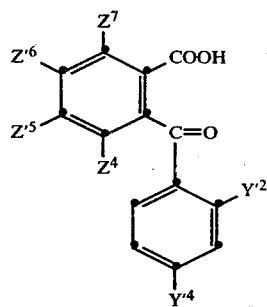

Formula II wherein:

$Y'^2$ is dialkylamino wherein alkyl is non-tertiary alkyl of one to four carbon atoms, alkanoylamino of two to five carbon atoms, or non-tertiary alkoxy of one to four carbon atoms;

$Y'^4$ is the same as $Y'^2$ when $Y'^2$ is dialkylamino; or dialkylamino, pyrrolidino, piperidino, morpholino, alkylbenzylamino, alkyl(4-alkoxyphenyl)amino or alkyl-(Q'-(CH$_2$)$_n$)amino, wherein alkyl is non-tertiary alkyl of one to four carbon atoms, alkoxy is non-tertiary alkoxy of one to four carbon atoms, Q' is chloro and n is two to four when $Y'^2$ is other than dialkylamino;

$Z^4$ is hydrogen or halo;

$Z'^5$ is hydrogen or halo; or dialkylamino wherein alkyl is non-tertiary alkyl of one to four carbon atoms when $Z^4$, $Z'^6$ and $Z^7$ are each hydrogen;

$Z'^6$ is hydrogen or halo; or dialkylamino wherein alkyl is non-tertiary alkyl of one to four carbon atoms when $Z^4$, $Z'^5$ and $Z^7$ are each hydrogen;

$Z^7$ is hydrogen or halo and acid addition salts thereof.

The compounds of Formula II are useful as intermediates in the following processes for preparing compounds of Formula I.

In one of its process aspects the invention provides the process for preparing 3-(2-X-4-X-phenyl)-3-(2-$Y^2$-4-$Y''^4$-phenyl)-4-$Z^4$-5-$Z''^5$-6-$Z''^6$-7-$Z^7$-phthalide of the formula

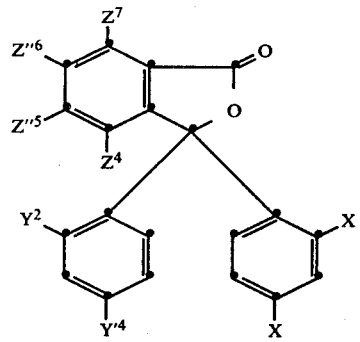

Formula III which comprises condensing 2-(2-$Y^2$-4-$Y''^4$-benzoyl)-3-$Z^4$-4-$Z''^5$-5-$Z''^6$-6-$Z^7$-benzoic acid of the formula

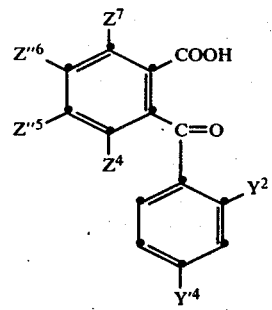

Formula IV with 1-X-3-X-benzene of the formula

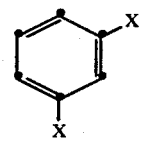

Formula V in contact with the anhydride of an alkanoic acid of two to five carbon atoms, phosphorus oxychloride or thionyl chloride, wherein:

X is dialkylamino wherein alkyl is non-tertiary alkyl of one to four carbon atoms;

$Y^2$ is hydrogen, non-tertiary alkyl of one to four carbon atoms, dialkylamino wherein alkyl is non-tertiary alkyl of one to four carbon atoms, alkanoylamino of two to five carbon atoms, non-tertiary alkoxy of one to four carbon atoms or halo;

$Y''^4$ is the same as $Y^2$ when $Y^2$ is dialkylamino; or dialkylamino, pyrrolidino, piperidino, morpholino, alkylbenzylamino, alkyl(4-alkoxyphenyl)amino or alkyl(Q'-(CH$_2$)$_n$)amino, wherein alkyl is non-tertiary alkyl of one to four carbon atoms, alkoxy is non-tertiary alkoxy of one to four carbon atoms, Q' is chloro and n is two to four when $Y^2$ is other than dialkylamino;

$Z^4$ is hydrogen or halo;

$Z''^5$ is hydrogen or halo; or non-tertiary alkyl of one to four carbon atoms, nitro, dialkylamino wherein alkyl is non-tertiary alkyl of one to four carbon atoms when $Z^4$, $Z''^6$ and $Z^7$ are each hydrogen;

$Z''^6$ is hydrogen or halo; or non-tertiary alkyl of one to four carbon atoms, nitro, dialkylamino wherein alkyl is non-tertiary alkyl of one to four carbon atoms when $Z^4$, $Z''^5$ and $Z^7$ are each hydrogen; and $Z^7$ is hydrogen or halo.

In its other process aspect the invention provides the process for preparing 3-(2-X-4-X-phenyl)-3-(2-$Y^2$-4-$Y'^4$-phenyl)-4-$Z^4$-5-$Z''^5$-6-$Z''^6$-7-$Z^7$-phthalide of Formula III which comprises condensing 2-(2-X-4-X-benzoyl)-3-$Z^4$-4-$Z''^5$-5-$Z''^6$-6-$Z^7$-benzoic acid of the formula

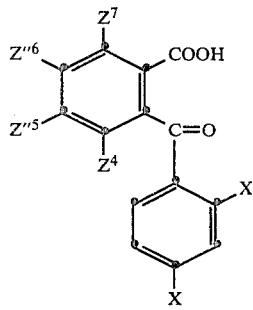

Formula VI with 1-$Y^2$-3-$Y'^4$-benzene of the formula

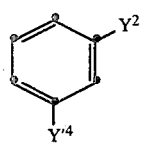

Formula VII in contact with the anhydride of an alkanoic acid of two to five carbon atoms, phosphorus oxychloride or thionyl chloride, wherein:

X is dialkylamino wherein alkyl is non-tertiary alkyl of one to four carbon atoms;

$Y^2$ is hydrogen, non-tertiary alkyl of one to four carbon atoms, dialkylamino wherein alkyl is non-tertiary alkyl of one to four carbon atoms, alkanoylamino of two to five carbon atoms, non-tertiary alkoxy of one to four carbon atoms or halo;

$Y'^4$ is the same as $Y^2$ when $Y^2$ is dialkylamino; or dialkylamino, pyrrolidino, piperidino, morpholino, alkylbenzylamino, alkyl(4-alkoxyphenyl)amino or alkyl(Q'-(CH$_2$)$_n$)amino, wherein alkyl is non-tertiary alkyl of one to four carbon atoms, alkoxy is non-tertiary alkoxy of one to four carbon atoms, Q' is chloro and n is two to four when $Y^2$ is other than dialkylamino;

$Z^4$ is hydrogen or halo;

$Z''^5$ is hydrogen or halo; or non-tertiary alkyl of one to four carbon atoms, nitro, dialkylamino wherein alkyl is non-tertiary alkyl of one to four carbon atoms when $Z^4$, $Z''^6$ and $Z^7$ are each hydrogen;

$Z\Delta^6$ is hydrogen or halo; or non-tertiary alkyl of one to four carbon atoms, nitro, dialkylamino wherein alkyl is non-tertiary alkyl of one to four carbon atoms when $Z^4$, $Z''^5$ and $Z^7$ are each hydrogen; and $Z^7$ is hydrogen or halo.

The foregoing two process aspects of the invention do not provide directly the compounds of Formula I wherein $Y^4$ is alkyl(Q-(CH$_2$)$_n$)amino wherein Q is hydroxy. However, such compounds are provided by carrying out either of the process aspects of the invention with the appropriate intermediates wherein Q is hydroxy and the anhydride of an alkanoic acid of two to five carbon atoms as the condensing agent, and dealk-anoylating the resulting product wherein Q is the corresponding alkanoyloxy of two to five carbon atoms.

Nor do the foregoing two process aspects of the invention provide directly the compounds of Formula I wherein $Z^5$ or $Z^6$ is amino. However, such compounds are provided by carrying out either of the process aspects of the invention with the appropriate intermediates wherein $Z^5$ and $Z^6$ is amino and, if the anhydride of an alkanoic acid of two to five carbon atoms is used as the condensing agent, dealkanoylating the resulting product wherein $Z^5$ or $Z^6$ is the corresponding alkanoylamino of two to five carbon atoms.

In one of its system aspects the invention provides a pressure-sensitive duplicating system comprising a support sheet having a coat of pressure-rupturable carboxymethylcellulose-gelatin microcapsules containing an oil solution of a compound of Formula I.

In its other system aspect the invention provides a heat-sensitive marking system comprising a support sheet having a coat of a mixture of a polyvinyl alcohol dispersion of a phenolic material and a polyvinyl alcohol dispersion of a compound of Formula I.

DETAILED DESCRIPTION OF THE INVENTION

Definitions

Non-tertiary alkyl of one to four carbon atoms is methyl, ethyl, propyl, isopropyl, butyl, isobutyl or sec-butyl.

Alkanoylamino of two to five carbon atoms is acetamido, propionamido, butyrylamino, isobutyrylamino, valerylamino, isovalerylamino, α-methylbutyrylamino or pivaloylamino.

Non-tertiary alkoxy of one to four carbon atoms is methoxy, ethoxy, propoxy, isopropoxy, butoxy, isobutoxy or sec-butoxy.

Halo is fluoro, chloro, bromo or iodo.

The anhydrides of alkanoic acids of two to five carbon atoms are acetic anhydride, propionic anhydride, butyric anhydride, isobutyric anhydride, valeric anhydride, isovaleric anhydride, α-methylbutyric anhydride and pivalic anhydride.

Preparation of Final Products

In carrying out the processes of the invention a mixture of 2-(2-$Y^2$-4-$Y'^4$-benzoyl)-3-$Z^4$-4-$Z''^5$-5-$Z''^6$-6-$Z^7$-benzoic acid of Formula IV and 1-X-3-X-benzene of Formula V or a mixture of 2-(2-X-4-X-benzoyl)-3-$Z^4$-4-$Z''^5$-5-$Z''^6$-6-$Z^7$-benzoic acid of Formula VI and 1-$Y^2$-3-$Y'^4$-benzene of Formula VII and the anhydride of an alkanoic anhydride, preferably acetic anhydride, phosphorus oxychloride or thionyl chloride with or without an inert diluent, is heated at a temperature in the range of 30°–150° C. In some cases the product of Formula III precipitates from the resulting mixture and may be isolated directly. Otherwise the resulting mixture is first acidified with a dilute aqueous mineral acid, for example, hydrochloric acid, and then basified, for example, with dilute aqueous sodium hydroxide, and the product is then isolated.

The compounds of Formula I wherein $Z^5$ or $Z^6$ is amino are alternatively provided by reduction of the corresponding compounds of Formula I wherein $Z^5$ or $Z^6$ is nitro with, for example, stannous chloride.

The compounds of Formula I wherein $Z^5$ or $Z^6$ is nitro are alternatively provided by nitration of the corresponding compounds of Formula I wherein $Z^5$ and $Z^6$ are hydrogen with, for example, a mixture of nitric acid and sulfuric acid. The nitration can produce the 5-nitro isomer, the 6-nitro isomer or a mixture of both.

The compounds of Formula I wherein $Z^5$ or $Z^6$ is halo are alternatively provided by halogenation of the diazonium salts derived from the corresponding compounds of Formula I wherein $Z^5$ or $Z^6$ is amino with, for example, fluoroboric acid, cuprous chloride, cuprous bromide or potassium iodide.

Preparation of Intermediates

The compounds of Formula IV and Formula VI, which include among them the compounds of Formula II, are prepared by condensing the corresponding 3-$Z^4$-4-$Z'''^5$-5-$Z'''^6$-6-$Z^7$-phthalic anhydrides of the formula

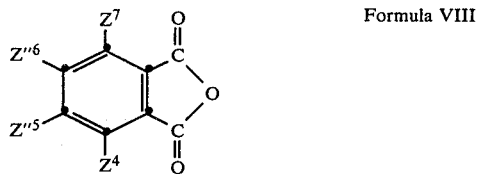

Formula VIII with the corresponding 1-$Y^2$-3-$Y'^4$-benzenes of Formula VII or 1-$X$3-$X$-benzenes of Formula V, respectively, in contact with a Lewis acid, for example, aluminum chloride or zinc chloride, and with a diluent, for example, benzene, chlorobenzene or o-dichlorobenzene, at a temperature in the range of 20°–200° C. This condensation can produce isomers or mixtures of isomers when the $Z'''^5$ or $Z'''^6$ substituent of the compounds of Formula VIII is alkyl, nitro, dialkylamino or halo. Thus the derived compounds of Formula IV and Formula VI have the substituent at the 4-position of the 5-position. Compounds of Formula IV or Formula VI having the substituent in the 4-position or the 5-position produce the corresponding compounds of Formula I having the substituent in the 5-position or the 6-position.

Acid addition salts of the compounds of Formula II, Formula IV and Formula VI can be prepared with inorganic (mineral) or organic acids. If inorganic, the acid can be, for example, hydrochloric acid, hydrobromic acid, nitric acid, phosphoric acid, sulfuric acid or sulfamic acid. If organic, the acid can be, for example, acetic acid, glycolic acid, lactic acid, quinic acid, hydrocinnamic acid, succinic acid, tartaric acid, citric acid, methanesulfonic acid or benzenesulfonic acid.

The molecular structures of the compounds of Formula I, Formula II, Formula IV and Formula VI follow from the structures of the compounds of Formula V, Formula VII and Formula VIII and the synthetic method and may be identified and corroborated by observation of one or more of the following physical properties: color, melting point (m.p.), solubility behavior, acid-base behavior, thin layer chromatographic spectrum, infrared spectrum, mass spectrum, nulcear magnetic resonance spectrum and ultraviolet spectrum.

The compounds of Formula VIII wherein $Z^4$ is halo and $Z'''^5$ or $Z'''^6$ is nitro or halo are known. Some of the compounds of Formula VIII wherein $Z'''^5$ or $Z'''^6$ is dialkylamino are also known. Those which are not known can be prepared, for example, according to the method of U.S. Pat. No. 2,597,965 starting with diethyl 4-aminophthalate and, successively, appropriately N-alkylating, de-ethylating and cyclizing.

Some of the compounds of Formula V and the compounds of Formula VII wherein $Y^2$ is dialkylamino are known. Those which are not known can be prepared, for example, by appropriately N-alkylating m-phenylenediamine.

Some of the compounds of Formula VII wherein $Y^2$ is hydrogen are known. Those which are not known can be prepared by appropriately N-alkylating aniline. Julolidine is known.

Some of the compounds of Formula VII wherein $Y^2$ is alkyl are known. Those which are not known can be prepared, for example, starting with the appropriate alkylbenzene and, successively, 4-nitrating, reducing the nitro to amino, N-acetylating, 3-nitrating, deacetylating, deaminating, reducing the nitro to amino and appropriately N-alkylating.

Some of the compounds of Formula VII wherein $Y^2$ is alkanoylamino are known. Those which are not known can be prepared, for example, starting with m-nitroaniline and, successively, N-alkanoylating, reducing the nitro to amino and appropriately N-alkylating.

Some of the compounds of Formula VII wherein $Y^2$ is alkoxy are known. Those which are not known can be prepared, for example, starting with m-hydroxyacetanilide and, successively, appropriately O-alkylating, deacetylating and appropriately N-alkylating.

The foregoing methods also provide the corresponding compounds of Formula VII wherein $Y'^4$ is alkyl(hydroxy-$(CH_2)_n$)-amino which are not known.

Preparation of Systems

Preparation of pressure-sensitive duplicating systems by carboxymethylcellulose-gelatin microencapsulation of the compounds of Formula I is accomplished by the method described in U.S. Pat. No. 3,649,649. A preferred oil for dissolving the color precursor is isopropylbiphenyl. Preparation of heat-sensitive marking systems by polyvinyl alcohol dispersion of the compounds of Formula I is accomplished by the method described in U.S. Pat. No. 3,539,375. A preferred phenolic material is bisphenol A.

EXAMPLES

EXAMPLE 1

A. A mixture of phthalic anhydride (30 g.), N,N-dimethylaniline (60.5 g.), aluminum chloride (60 g.) and chlorobenzene (180 g.) was heated (to 75° C.) during one hour, then cooled. Ice (50 ml.) was added, the chlorobenzene layer was separated and the chlorobenzene was steam distilled. Addition of base to a solution of the residue in dilute sulfuric acid afforded 2-(4-dimethylamino)benzoyl)benzoic acid (IV: $Y^2 = Z^4 = Z'''^5 = Z'''^6 = Z^7 = H$, $Y'^4 = (CH_3)_2N$).

B. A mixture of 2-(4-(dimethylamino)benzoyl)benzoic acid (26.8 g.), N,N,N',N'-tetramethyl-m-phenylenediamine (16.4 g.) and acetic anhydride (80 g.) was heated (to 95° C.) during one hour, cooled and poured into dilute hydrochloric acid. The resulting mixture was basified. Recrystallization of the resulting solid from a mixture of toluene and hexane afforded 3-(2,4-bis(dimethylamino)phenyl)-3-(4-(dimethylamino)-phenyl)phthalide (I: $X = Y^4 = (CH_3)_2N$, $Y^2 = Z^4 = Z^5 = Z^6 = Z^7 = H$) (m.p. 190°–194° C.).

When applied to acidic clay 3-(2,4-bis(dimethylamino)phenyl)-3-(4-(dimethylamino)phenyl)phthalide formed a gray-black image which was xerographically copiable.

C. Substituting N,N,N',N'-tetra(sec-butyl)-m-phenylenediamine (prepared by N-alkylating m- phenylenediamine with sec-butyl bromide) for N,N,N',N'-tetramethyl-m-phenylenediamine in part B of this example, there is obtained 3-(2,4-bis(di-sec-butylamino)phenyl)-3-(4-dimethylamino)phenyl)phthalide (I: X=(CH$_3$CH$_2$(CH$_3$)CH)$_2$N, Y$^2$=Z$^4$=Z$^5$=Z$^6$=Z$^7$=H, Y$^4$=(CH$_3$)$_2$N).

D. Condensation of 2-(2,4-bis(dimethylamino)benzoyl)benzoic acid and N,N-dimethylaniline in the presence of acetic anhydride also afforded 3-(2,4-bis(dimethylamino)phenyl)-3-(4-(dimethylamino)phenyl)phthalide.

EXAMPLE 2

A. A mixture of phthalic anhydride (60 g.), N,N-diethyl-m-toluidine (162.8 g.), aluminum chloride (120 g.) and chlorobenzene (360 ml.) was heated (75°–95° C.) during one and one-half hours, then diluted with water (200 ml., then more). More chlorobenzene (200 ml.) was added and the chlorobenzene layer was separated and steam distilled. Addition of sodium hydroxide solution (10%) to a solution of the residue in dilute sulfuric acid (20%, 250 ml.) afforded 2-(2-methyl-4-(diethylamino)benzoyl)benzoic acid (IV: Y$^2$=CH$_3$, Y'$^4$=(CH$_3$CH$_2$)$_2$N, Z$^4$=Z''$^5$=Z''$^6$=Z$^7$=H).

B. A mixture of 2-(2-methyl-4-(diethylamino)benzoyl)benzoic acid (25 g.), N,N,N',N'-tetramethyl-m-phenylenediamine (13.2 g.) and acetic anhydride (75 g.) was heated (to 95° C.) during one hour, then refluxed with dilute hydrochloric acid (32 g. concentrated hydrochloric acid plus 160 ml. water) during one and one-half hours. The resulting mixture was poured onto ice and the pH was adjusted to 6 with sodium hydroxide. Recrystallization of the resulting product afforded 3-(2,4-bis(dimethylamino)phenyl)-3-(2-methyl-4-(diethylamino)phenyl)phthalide (I: X=(CH$_3$)$_2$N, Y$^2$=CH$_3$, Y$^4$=(CH$_3$CH$_2$)$_2$N, Z$^4$=Z$^5$=Z$^6$=Z$^7$=H) in a first crop from toluene (m.p. 204°–206° C.) and in a second crop from a mixture of toluene and hexane (m.p. 191°–195° C.).

When applied to acidic clay 3-(2,4-bis(dimethylamino)phenyl)-3-(2-methyl-4-(diethylamino)phenyl)phthalide formed a violet-gray image which was xerographically copiable.

C. Substituting m-butyl-N,N-dimethylaniline (prepared by N-methylating m-butylaniline with dimethyl sulfate) for N,N-diethyl-m-toluidine in part A of this example, there is obtained 2-(2-butyl-4-(dimethylamino)benzoyl)benzoic acid (IV: Y$^2$=CH$_3$CH$_2$CH$_2$CH$_2$, Y'$^4$=(CH$_3$)$_2$N, Z$^4$=Z''$^5$=Z''$^6$=Z$^7$=H).

D. Substituting 2-(2-butyl-4-(dimethylamino)benzoyl)benzoic acid for 2-(2-methyl-4-(diethylamino)benzoyl)benzoic acid in part B of this example, there is obtained 3-(2,4-bis(dimethylamino)phenyl)-3-(2-butyl-4-(dimethylamino)phenyl)phthalide (I: X=Y$^4$=(CH$_3$)$_2$N, Y$^2$=CH$_3$CH$_2$CH$_2$CH$_2$, Z$^4$=Z$^5$=Z$^6$=Z$^7$=H).

E. Condensation of 2-(2,4-bis(dimethylamino)benzoyl)benzoic acid and N,N-diethyl-m-toluidine in the presence of acetic anhydride also afforded 3-(2,4-bis(-dimethylamino)phenyl)-3-(2-methyl-4-(diethylamino)phenyl)phthalide.

EXAMPLE 3

A. A mixture of phthalic anhydride (5.92 g.), N,N,N',N'-tetramethyl-m-phenylenediamine (6.56 g.), zinc chloride (5.40 g.) and chlorobenzene (70 ml.) was heated under reflux for three hours. The chlorobenzene was decanted and the residue was air-dried. A solution of the residue in dilute hydrochloric acid (10%, 20 ml. plus 20 ml. of water) was diluted with more water (20 ml.), affording 2-(2,4-bis(dimethylamino)benzoyl)benzoic acid (II: Y'$^2$=Y'$^4$=(CH$_3$)$_2$N, Z$^4$=Z'$^5$=Z'$^6$=Z$^7$=H) dihydrochloride trihydrate (4 g., m.p. 136°–141° C.; after recrystallization from ethanol, m.p. 140°–141° C.). In another preparation the free base (m.p. 165°–168° C.) was obtained under less acidic conditions (pH 4–6).

B. A mixture of crude 2-(2,4-bis(dimethylamino)benzoyl)benzoic acid (7 g.), N,N,N',N'-tetramethyl-m-phenylenediamine (1.64 g.) and acetic anhydride was warmed (at 25°–35° C.) during two to three hours, then poured into dilute hydrochloric acid (10%). The resulting mixture was basified and filtered with a filter aid. The filter cake was extracted with hot toluene. Dilution of the toluene extract with hexane afforded 3,3-bis(2,4-bis(dimethylamino)phenyl)phthalide (I: X=Y$^2$=Y$^4$=(CH$_3$)$_2$N, Z$^4$=Z$^5$=Z$^6$=Z$^7$=H) (m.p. 186°–188° C.).

When applied to silica gel or standard field resin 3,3-bis(2,4-dimethylamino)phenyl)phthalide formed a red-brown image which was xerographically copiable.

C. Substituting N,N,N',N'-tetra(sec-butyl)-m-phenylenediamine for N,N,N',N'-tetramethyl-m-phenylenediamine in part A of this example, there is obtained 2-(2,4-bis(di-sec-butylamino)benzoyl)benzoic acid (II: Y'$^2$=Y'$^4$=(CH$_3$CH$_2$—(CH$_3$)CH)$_2$N, Z$^4$=Z'$^5$=Z'$^6$=Z$^7$=H).

D. Substituting N,N-diethyl-m-toluidine for N,N,N',N'-tetramethyl-m-phenylenediamine in part B of this example, there is obtained 3-(2,4-bis(dimethylamino)phenyl)-3-(2-methyl-4-(diethylamino)phenyl)phthalide, the compound of part B of Example 2.

E. Substituting N-phenylpyrrolidine, N-phenylpiperidine or N-ethyl-N-(3-chloropropyl)aniline for N,N,N',N'-tetramethyl-m-phenylenediamine in part B of this example, there are obtained, respectively, 3-(2,4-bis(dimethylamino)phenyl)-3-(4-pyrrolidinophenyl)phthalide (I: X=(CH$_3$)$_2$N, Y$^2$=Z$^4$=Z$^5$=Z$^6$=Z$^7$=H,

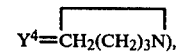
Y$^4$=CH$_2$(CH$_2$)$_3$N), 3-(2,4-bis-(dimethylamino)phenyl)-3-(4-piperidinophenyl)phthalide (I: X=(CH$_3$)$_2$N, Y$^2$=Z$^4$=Z$^5$=Z$^6$=Z$^7$=H,

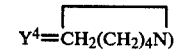
Y$^4$=CH$_2$(CH$_2$)$_4$N)

and 3-(2,4-bis(dimethylamino)phenyl)-3-(4-(ethyl(3-chloropropyl)amino)phenyl)phthalide (I: X=(CH$_3$)$_2$N, Y$^2$=Z$^4$=Z$^5$=Z$^6$=Z$^7$=H, Y$^4$=CH$_3$CH$_2$(Cl(CH$_2$)$_2$)N).

EXAMPLE 4

A. A mixture of 2-(2,4-bis(dimethylamino)benzoyl)benzoic acid (2.4 g.), m-(dimethylamino)acetanilide (1.42 g.) and acetic anhydride (20 ml.) was stirred at room temperture during two hours, filtered, diluted with dilute hydrochloric acid (10%) and made alkaline. Recrystallization of part of the resulting produce from a mixture of toluene, ligroin and hexane and part from a mixture of ethyl acetate and hexane afforded 3-(2,4-bis(-dimethylamino)phenyl)-3-(2-acetamido-4-(dimethylamino)phenyl)phthalide (I: $X=Y^4=(CH_3)_2N$, $Y^2=CH_3CONH$, $Z^4=Z^5=Z^6=Z^7=H$) (m.p. 97°–136° C.).

When applied to standard field resin 3-(2,4-bis(dimethylamino)phenyl)-3-(2-acetamido-4-(dimethylamino)-phenyl)phthalide formed a red-blue-brown image which was xerographically copiable.

B. Substituting m-(dimethylamino)-2,2-dimethylpropionanilide (prepared by N-alkanoylating N,N-dimethylphenylenediamine with pivaloyl chloride) for m-(dimethylamino)acetanilide in part A of this example, there is obtained 3-(2,4-bis(dimethylamino)phenyl)-3-(2-pivaloylamino-4-(dimethylamino)phenyl)phthalide (I: $X=Y^4=(CH_3)_2N$, $Y^2=(CH_3)_3CCONH$, $Z^4=Z^5=Z^6=Z^7=H$).

C. Condensation of phthalic anhydride and m-(dimethylamino)acetanilide by the method of part A of Example 1 affords 2-(2-acetamido-4-(dimethylamino)benzoyl)benzoic acid (II: $Y'^2=CH_3CONH$, $Y'^4=(CH_3)_2N$, $Z^4=Z'^5=Z'^6=Z^7=H$).

D. Condensation of 2-(2-acetamido-4-(dimethylamino)benzoyl)benzoic acid and N,N,N',N'-tetramethyl-m-phenylenediamine by the method of part B of Example 1 affords 3-(2,4-bis(dimethylamino)phenyl)-3-(2-acetamido-4-(dimethylamino)phenyl)phthalide, the compound of part A of this example.

EXAMPLE 5

A. A mixture of phthalic anhydride (15 g.), m-ethoxy-N,N-diethylaniline (19 g.), aluminum chloride (15 g.) and o-dichlorobenzene (90 g.) was heated (to 75° C.) during one hour, then diluted with ice-water. The o-dichlorobenzene layer was separated and steam distilled. Adjustment to pH 5 of a solution of the residue in dilute sulfuric acid (10%, 100 ml.) afforded 2-(2-ethoxy-4-(diethylamino)benzoyl)benzoic acid (II: $Y'^2=CH_3CH_2O$, $Y'^4=(CH_3CH_2)_2N$, $Z^4=Z'^5=Z'^6=Z^7=H$) (11 g., m.p. 174°–181° C.).

B. A mixture of 2-(2-ethoxy-4-(diethylamino)benzoyl)benzoic acid (6.82 g.), N,N,N',N'-tetramethyl-m-phenylenediamine (2.80 g.) and acetic anhydride (20 g.) was heated (70°–75° C.) during one hour, let stand overnight and poured into dilute hydrochloric acid. The resulting mixture was basified. Recrystallization of the resulting red precipitate from hexane followed by slurrying in alkaline water afforded 3-(2,4-bis(dimethylamino)phenyl)-3-(2-ethoxy-4-(diethylamino)-phenyl)phthalide (I: $X=(CH_3)_2N$, $Y^2=CH_3CH_2O$, $Y^4=(CH_3CH_2)_2N$, $Z^4=Z^5=Z^6=Z^7=H$) (m.p. 146°–150° C.).

When applied to acidic clay 3-(2,4-bis(dimethylamino)phenyl)-3-(2-ethoxy-4-(diethylamino)-phenyl)phthalide formed a blue-black image which was xerographically copiable.

C. Substituting m-isobutoxy-N,N-dimethylaniline (prepared by O-alkylating m-hydroxyacetanilide with isobutyl bromide, then deacetylating the resulting m-isobutoxyacetanilide, then N-alkylating the resulting m-isobutoxyaniline with methyl sulfate) for m-ethoxy-N,N-diethylaniline in part A of this example, there is obtained 2-(2-isobutoxy-4-(dimethylamino)benzoyl)-benzoic acid (II: $Y'^2=(CH_3)_2CHCH_2O$, $Y'^4=(CH_3)_2N$, $Z^4=Z'^5=Z'^6=Z^7=H$).

D. Substituting 2-(2-isobutoxy-4-(dimethylamino)-benzoyl)benzoic acid for 2-(2-ethoxy-4-(diethylamino)-benzoyl)benzoic acid in part B of this example, there is obtained 3-(2,4-bis(dimethylamino)phenyl)-3-(2-isobutoxy-4-(dimethylamino)phenyl)phthalide (I: $X=(CH_3)_2N$, $Y^2=(CH_3)_2CHCH_2O$, $Y^4=(CH_3)_2N$, $Z^4=Z^5=Z^6=Z^7=H$).

E. Condensation of phthalic anhydride and N-(m-anisyl)pyrrolidine (prepared from m-anisidine and 1,4-dibromobutane), N-(m-anisyl)piperidine (prepared from m-anisidine and 1,5-dibromopentane) or N-methyl-N-(2-chloroethyl)-m-anisidine (prepared from N-methyl-m-anisine and 1-bromo-2-chloroethane) by the method of part A of Example 1 affords, respectively, 2-(2-methoxy-4-pyrrolidinobenzoyl)benzoic acid (II: $Y'^2=CH_3O$,

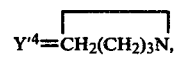

$Z^4=Z'^5=Z'^6=Z^7=H$), 2-(2-methoxy-4-piperidinobenzoyl)benzoic acid (II: $Y'^2=CH_3O$,

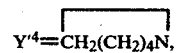

$Z^4=Z'^5=Z'^6=Z^7=H$) and 2-(2-methoxy-4-(methyl(2-chloroethyl)amino)benzoyl)benzoic acid (II: $Y'^2=CH_3O$, $Y'^4=CH_3(ClCH_2CH_2)N$, $Z^4=Z'^5=Z'^6=Z'^7=H$).

F. Condensation of 2-(2-methoxy-4-pyrrolidinobenzoyl)benzoic acid, 2-(2-methoxy-4-piperidinobenzoyl)-benzoic acid or 2-(2-methoxy-4-(methyl(2-chloroethyl))amino)benzoyl)benzoic acid with N,N,N',N'-tetramethyl-m-phenylenediamine by the method of part B of Example 1 affords, respectively, 3-(2,4-bis(dimethylamino)phenyl)-3-(2-methoxy-4-pyrrolidino-phenyl)phthalide (I: $X=(CH_3)_2N$, $Y^2=CH_3O$,

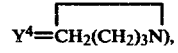

$Z^4=Z^5=Z^6=Z^7=H$), 3-(2,4-bis(dimethylamino)-phenyl)-3-(2-methoxy-4-piperidinophenyl)phthalide (I: $X=(CH_3)_2N$, $Y^2=CH_3O$,

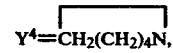

$Z^4=Z^5=Z^6=Z^7=H$) and 3-(2,4-bis(dimethylamino)-phenyl)-3-(2-methoxy-4-(methyl(2-chloroethyl)amino)-phenyl)phthalide (I: $X=(CH_3)_2N$, $Y^2=CH_3O$, $Y^4=CH_3)ClCH_2CH_2)N$, $Z^4=Z^5=Z^6=Z^7=H$).

EXAMPLE 6

A. A mixture of tetrachlorophthalic anhydride (21.4 g.), N,N-diethyl-m-toluidine (41 g.), aluminum chloride (30 g.) and o-dichlorobenzene (90 ml.) was heated (75°–95° C.) during one to two hours, then diluted with ice-water. The o-dichlorobenzene layer was separated and steam distilled. The residue was heated with dilute sulfuric acid. The mixture was poured onto ice and made alkaline. The resulting oil was heated in concentrated sulfuric acid. Dilution with water and purification of the product with toluene and hexane afforded 2-(2-methyl-4-(diethylamino)benzoyl)-3,4,5,6-tetrachlorobenzoic acid (IV: $Y^2=CH_3$, $Y'^4=(CH_3CH_2)_2N$, $Z^4=Z''^5=Z''^6=Z^7=Cl$) (26 g., m.p. 117° C. with sublimation).

B. A mixture of 2-(2-methyl-4-(diethylamino)benzoyl)-3,4,5,6-tetrachlorobenzoic acid (22.4 g.), N,N,N',N'-tetramethyl-m-phenylenediamine (8.20 g.) and acetic anhydride (75 g.) was heated (to 95° C.) during one to two hours, then refluxed with dilute hydrochloric acid (32 g. concentrated hydrochloric acid plus 160 ml. water) during one and one-half hours. The resulting mixture was poured into water and the pH was adjusted. Recrystallization of the resulting product from toluene afforded 3-(2,4-bis(dimethylamino)-phenyl)-3-(2-methyl-4-(diethylamino)phenyl)-4,5,6,7-tetrachlorophthalide (I: $X=(CH_3)_2N$, $Y^2=CH_3$, $Y^4=(CH_3CH_2)_2N$, $Z^4=Z^5=Z^6=Z^7=Cl$) (m.p. 236°–238° C.; after slurrying in acetone, 237°–239° C.).

When applied to acidic clay 3-(2,4-bis(dimethylamino)phenyl)-3-(2-methyl-4-(diethylamino)-phenyl)-4,5,6,7-tetrachlorophthalide formed an image which was xerographically copiable.

EXAMPLE 7

A. A mixture of tetrachlorophthalic anhydride (1.92 g.), N,N,N',N'-tetramethyl-m-phenylenediamine (1.64 g.), zinc chloride (1.35 g.) and chlorobenzene (40–45 ml.) was heated under reflux during three hours. The chlorobenzene layer was decanted and the residue was slurried with dilute hydrochloric acid (10%, 20 ml.) and water (20 ml.), affording 2-(2,4-bis(dimethylamino)benzoyl)-3,4,5,6-tetrachlorobenzoic acid (II: $Y'^2=Y'^4=(CH_3)_2N$, $Z^4=Z'^5=Z'^6=Z^7=Cl$) (m.p. 199°–201° C.).

B. A mixture of most of the 2-(2,4-bis(dimethylamino)benzoyl)-3,4,5,6-tetrachlorobenzoic acid from part A of this example, N,N,N',N'-tetramethyl-m-phenylenediamine (0.82 g. plus 0.4 g.) and acetic anhydride was heated under reflux. Concentration of a toluene extract of the resulting product gave a tar, which was slurried in hexane, affording 3,3-bis(2,4-bis(dimethylamino)phenyl)-4,5,6,7-tetrachlorophthalide (I: $X=Y^2=Y^4=(CH_3)_2N$, $Z^4=Z^5=Z^6=Z^7=Cl$) (m.p. 195°–197° C.).

When applied to acidic clay 3,3-bis(2,4-bis(dimethylamino)phenyl)-4,5,6,7-tetrachlorophthalide formed a red-blue image which was xerographically copiable.

C. Substituting tetrafluorophthalic anhydride, tetrabromophthalic anhydride or tetraiodophthalic anhydride for tetrachlorophthalic anhydride in part A of this example, there are obtained, respectively, 2-(2,4-bis(dimethylamino)benzoyl)-3,4,5,6-tetrafluorobenzoic acid (II: $Y'^2=Y'^4=(CH_3)_2N$, $Z^4=Z'^5=Z'^6=Z^7=F$), 2-(2,4-bis(dimethylamino)benzoyl)-3,4,5,6-tetrabromobenzoic acid (II: $Y^2=Y'^4=(CH_3)_2N$, $Z^4=Z'^5=Z'^6=Z^7=Br$) and 2-(2,4-bis(dimethylamino)benzoyl)-3,4,5,6-tetraiodobenzoic acid (II: $Y'^2=Y'^4=(CH_3)_2N$, $Z^4=Z'^5=Z'^6=Z'^7=I$).

D. Substituting 2-(2,4-bis(dimethylamino)benzoyl)-3,4,5,6-tetrafluorobenzoic acid, 2-(2,4-bis(dimethylamino)benzoyl)-3,4,5,6-tetrabromobenzoic acid or 2-(2,4-bis(dimethylamino)benzoyl)-3,4,5,6-tetraiodobenzoic acid for 2-(2,4-bis(dimethylamino)benzoyl)-3,4,5,6-tetrachlorobenzoic acid in part B of this example, there are obtained, respectively, 3,3-bis(2,4-bis(dimethylamino)phenyl)4,5,6,7-tetrafluorophthalide (I: $X=Y^2=Y^4=(CH_3)_2N$, $Z^4=Z^5=Z^6=Z^7=F$), 3,3-bis(2,4-bis(dimethylamino)phenyl)-4,5,6,7-tetrabromophthalide (I: $X=Y^2=Y^4=(CH_3)_2N$, $Z^4=Z^5=Z^6=Z^7=Br$) and 3,3-bis(2,4-bis(dimethylamino)phenyl)-4,5,6,7-tetraiodophthalide (I: $X=Y^2=Y^4=(CH_3)_2N$, $Z^4=Z^5=Z^6=Z^7=I$).

EXAMPLE 8

Three portions of a mixture of concentrated nitric acid (0.6 ml. each portion) and concentrated sulfuric acid (0.66 ml. each portion) were added to a mixture of 3-(2,4-bis(dimethylamino)phenyl)-3-(4-(dimethylamino)phenyl)phthalide (4.17 g.) and concentrated sulfuric acid (20 ml.) with cooling. After each addition the temperature was allowed to rise to room temperature. The resulting mixture was poured onto ice and the resulting mixture was basified, affording 3-(2,4-bis(dimethylamino)phenyl)-3-(4-(dimethylamino)phenyl5 or 6-nitrophthalide (I: $X=Y^4=(CH_3)_2N$, $Y^2=Z^4=Z^7=H$, $Z^5$ or $Z^6=O_2N$ and the other of $Z^5$ or $Z^6=H$) or a mixture of both.

When applied to silica gel 3-(2,4-bis(dimethylamino)phenyl)-3-(4-dimethylamino)phenyl)-5 or 6-nitrophthalide formed a gray-black image which was xerographically copiable.

EXAMPLE 9

In a manner similar to that of Example 8 nitration of 3-(2,4-bis(dimethylamino)phenyl)-3-(2-methyl-4-(diethylamino)phenyl)phthalide (4.57 g.) afforded 3-(2,4-bis(dimethylamino)phenyl)-3-(2-methyl-4-(diethylamino)phenyl5 or 6 nitrophthalide (I: $X=(CH_3)_2N$, $Y^2=CH_3$, $Y^4=(CH_3CH_2)_2N$, $Z^4=Z^7=H$, $Z^5$ or $Z^6=O_2N$ and the other of $Z^5$ or $Z^6=H$) or a mixture of both.

When applied to silica gel 3-(2,4-bis(dimethylamino)phenyl)-3-(2-methyl-4-(diethylamino)phenyl)-5 or 6-nitrophthalide formed a gray-black image which was xerographically copiable.

EXAMPLE 10

A. Stannous chloride dihydrate (6.7 g.) was added slowly to a mixture of most of the product of Example 8 and concentrated hydrochloric acid (50 ml.) with heating (60° C.). After one hour the resulting mixture was cooled, made alkaline and filtered, affording 3-(2,4-bis(dimethylamino)phenyl)-3-(4-(dimethylamino)-phenyl)-5 or 6-aminophthalide (I: $X=Y^4=(CH_3)_2N$, $Y^2=Z^4=Z^7=H$, $Z^5$ or $Z^6=H_2N$ and the other of $Z^5$ or $Z^6=H$) or a mixture of both.

When applied to silica gel 3-(2,4-bis(dimethylamino)phenyl-3-(4-(dimethylamino)phenyl)-5 or 6-aminophthalide formed a gray-violet or gray-brown image which was xerographically copiable.

B. Condensation of 4-aminophthalic anhydride and N,N,N',N'-tetramethyl-m-phenylenediamine by the method of part A of Example 3 affords 2-(2,4-bis(dimethylamino)benzoyl)5-aminobenzoic acid.

C. Condensation of 2-(2,4-bis(dimethylamino)benzoyl)5-aminobenzoic acid and N,N,N',N'-tetramethyl-m-phenylenediamine by the method of part B of Example 3 and deacetylation of the resulting product affords 3,3-(2,4-bis(dimethylamino)phenyl)-6-aminophthalide (I: $X=Y^2=Y^4=(CH_3)_2N$, $Z^4=Z^5=Z^7=H$, $Z^6=H_2N$).

EXAMPLE 11

In a manner similar to that of Example 10 reduction of most of the product of Example 9 afforded 3-(2,4-bis(dimethylamino)phenyl)-3-(2-methyl-4-(diethylamino)phenyl-5 or 6-aminophthalide (I: $X=(CH_3)_2N$, $Y^2=CH_3$, $Y^4=(CH_3CH_2)_2N$, $Z^4=Z^7=H$, $Z^5$ or $Z^6=H_2N$ and the other of $Z^5$ or $Z^6=H$) or a mixture of both.

When applied to silica gel 3-(2,4-bis(dimethylamino)phenyl)-3-(2-methyl-4-(diethylamino)phenyl)-5 or 6-aminophthalide formed a gray-violet or gray-black image which was xerographically copiable.

EXAMPLE 12

A. A mixture of 4-(dimethylamino)phthalic anhydride (7 g.), N,N-dimethylaniline (9.12 g.), aluminum chloride (11.7 g.) and benzene (36.5 ml.) was stirred (for 10 min.) at ice-bath temperature, then overnight at room temperature. The mixture was then extracted with dilute sulfuric acid (20%, 80 ml.). Adjustment of the pH of the acidic extract to 5 afforded a mixture of 2-(4-(dimethylamino)benzoyl)-4-(dimethylamino)benzoic acid (IV: $Y^2=Z^4=Z''^6=Z^7=H$, $Y'^4=Z''^5=(CH_3)_2N$) and 2-(4-(dimethylamino)benzoyl)-5-(dimethylamino)benzoic acid (IV: $Y^2=Z^4=Z''^5=Z^7=H$, $Y'^4=Z''^6=(CH_3)_2N$) (6.3 g.).

B. A mixture of part (3.12 g.) of the mixture of products from part A of this example, N,N,N',N'-tetramethyl-m-phenylenediamine (1.5 g.) and acetic anhydride (20 g.) was heated (to 85° C.), then cooled. The resulting precipitate was washed with ether, washed with alkali and recrystallized from acetone, affording 3-(2,4-bis(dimethylamino)phenyl-3-(4-(dimethylamino)phenyl)-5-(dimethylamino)phthalide (I: $X=Y^4=Z^5=(CH_3)_2N$, $Y^2=Z^4=Z^6=Z^7=H$) (m.p. 222°–225° C.).

When applied to acidic clay 3-(2,4-bis(dimethylamino)phenyl)-3-(4-dimethylamino)phenyl)-5-(dimethylamino)phthalide slowly formed a blue-gray image which was xerographically copiable.

C. The acetic anhydride filtrate from part B of this example was treated first with dilute hydrochloric acid (16 g. of concentrated acid plus 80 g. of water), then basified, affording 3-(2,4-bis(dimethylamino)phenyl)-3-(4-(dimethylamino)phenyl)-6-(dimethylamino)phthalide (I: $X=Y^4=Z^6=(CH_3)_2N$, $Y^2=Z^4=Z^5=Z^7=H$) (m.p. 182°–185° C. after purification).

When applied to acidic clay 3-(2,4-bis(dimethylamino)phenyl)-3-(4-(dimethylamino)phenyl)-6-(dimethylamino)phthalide rapidly formed a violet-purple image which was xerographically copiable.

D. Propionic anhydride, phosphorus oxychloride or thionyl chloride can be substituted for acetic anhydride in part B of this example.

EXAMPLE 13

A. A mixture of 4-(dimethylamino)phthalic anhydride (1.91 g.), N,N,N',N'-tetramethyl-m-phenylenediamine (1.64 g.), zinc chloride (2.70 g.) and chlorobenzene (50 ml.) was heated under reflux during two hours. The chlorobenzene layer was decanted and the residue was slurried in water (80 ml.) and dilute hydrochloric acid (10%, 4 drops), affording 2-(2,4-bis(dimethylamino)benzoyl)-4-(dimethylamino)benzoic acid (II: $Y'^2=Y'^4=Z'^5=(CH_3)_2N$, $Z^4=Z'^6=Z^7=H$) (m.p. 216°–222° C.) or the 5-(dimethylamino) isomer thereof.

B. A mixture of 2-(2,4-bis(dimethylamino)benzoyl)-4-(dimethylamino)benzoic acid or the 5-(dimethylamino) isomer thereof (10 g.), N,N,N'-tetramethyl-m-phenylenediamine (2.30 g.) and acetic anhydride (50 ml.) was warmed (at 30°–35° C.) during one hour. More N,N,N',N'-tetramethyl-m-phenylenediamine (1.15 g.) was added and warming was continued. The mixture was diluted with dilute hydrochloric acid (10%) and ice and filtered. The filtrate was made alkaline. Crystallization of the product from toluene afforded 3,3-bis(2,4-bis(dimethylamino)phenyl)-5-(dimethylamino)phthalide (I: $X=Y^2=Y^4=Z^5=(CH_3)_2N$, $Z^4=Z^6=Z^7=H$) (m.p. 188°–192° C.) or the 6-(dimethylamino) isomer thereof.

C. Substituting N-ethyl-N-(4-hydroxybutyl)aniline for N,N,N',N'-tetramethyl-m-phenylenediamine in part B of this example and deacetylating the resulting product, there is obtained 3-(2,4-bis(dimethylamino)phenyl)-3-(4-(ethyl(4-hydroxybutyl)amino)phenyl)-5-(dimethylamino)phthalide (I: $X=Z^5=(CH_3)_2N$, $Y^2=Z^4=Z^6=Z^7=H$, $Y^4=CH_3CH_2(HO(CH_2)_4)N$) or the 6-(dimethylamino) isomer thereof.

D. Substituting 4-methylphthalic anhydride, 4-nitrophthalic anhydride or 4-chlorophthalic anhydride for 4-(dimethylamino)phthalic anhydride in part A of this example, there are obtained, respectively, 2-(2,4-bis(dimethylamino)benzoyl)-5-methylbenzoic acid (VI: $X=(CH_3)_2N$, $Z^4=Z''^5=Z^7=H$, $Z''^6=CH_3$), 2-(2,4-bis(dimethylamino)benzoyl)-5-nitrobenzoic acid (VI: $X=(CH_3)_2N$, $Z^4=Z'^5=Z^7=H$, $Z'^6=O_2N$) and 2-(2,4-bis(dimethylamino)benzoyl-5-chlorobenzoic acid (VI: $X=(CH_3)_2N$, $Z^4=Z'^5=Z^7=H$, $Z'^6=Cl$).

E. Substituting 2-(2,4-bis(dimethylamino)benzoyl)-5-methylbenzoic acid, 2-(2,4-bis(dimethylamino)benzoyl)-5-nitrobenzoic acid or 2-(2,4-bis(dimethylamino)benzoyl)-5-chlorobenzoic acid for 2-(2,4-bis(dimethylamino)benzoyl)-5-(dimethylamino)benzoic acid in part B of this example, there are obtained, respectively, 3,3-bis(2,4-bis(dimethylamino)phenyl)-6-methylphthalide (I: $X=Y^2=Y^4=(CH_3)_2N$, $Z^4=Z^5=Z^7=H$, $Z^6=CH_3$) and 3,3-bis(2,4-bis(dimethylamino)phenyl)-6-nitrophthalide (I: $X=Y^2=Y^4=(CH_3)_2N$, $Z^4=Z^5=Z^7=H$, $Z^6=O_2N$) and 3,3-bis(2,4-bis(dimethylamino)phenyl)-6-chlorophthalide (I: $X=Y^2=Y^4=(CH_3)_2N$, $Z^4=Z^5=Z^7=H$, $Z^6=Cl$).

EXAMPLE 14

Sodium nitrite is added to a mixture of 3,3-bis(2,4-bis(dimethylamino)phenyl)-6-aminophthalide in dilute hydrobromic acid. The resulting mixture is added to a solution of cuprous bromide in dilute hydrobromic acid, affording, after basification, 3,3-bis(2,4-bis(dimethylamino)phenyl)-6-bromophthalide (I: $X=Y^2=Y^4=(CH_3)_2N$, $Z^4=Z^5=Z^7=H$, $Z^6=Br$).

EXAMPLE 15

A. A mixture of phthalic anhydride (30 g.), N,N-diethylaniline (71.6 g.), aluminum chloride (60 g.) and o-dichlorobenzene (200 ml.) was heated (to 75° C.), then diluted with ice (300 ml.) and water (500 ml.). The o-dichlorobenzene layer was separated and steam distilled. Addition of base to a solution of the residue in dilute sulfuric acid afforded 2-(4-diethylamino)benzoyl)benzoic acid (IV: $Y^2=Z^4$ $Z''^5=Z''^6=Z^7=H$, $Y'^4=(CH_3CH_2)_2N$) (58.9 g., m.p. 179°–181° C.).

B. A mixture of 2-(4-diethylamino)benzoyl)benzoic acid (5.94 g.), N,N,N',N'-tetramethyl-m-phenylenediamine (3.61 g.) and acetic anhydride (3 ml.) was warmed (to 45° C.). Addition of methanol (20 ml.) afforded 3-(2,4-bis(dimethylamino)phenyl)-3-(4-(diethylamino)phenyl)phthalide (I: $X=(CH_3)_2N$, $Y^2=Z^4=Z^5=Z^6=Z^7=H$, $Y^4=(CH_3CH_2)_2N$) (6.8 g., m.p. 168°–169.5° C.).

EXAMPLE 16

A mixture of 2-(4-dimethylamino)benzoyl)benzoic acid (8.07 g.), N,N,N',N'-tetraethyl-m-phenylenediamine (7.26 g.) and acetic anhydride (5 ml.) was heated (at 52° C.) during one and one-half hours. Addition of methanol (10 ml., then 15 ml.) afforded 3-(2,4-bis(diethylamino)phenyl)-3-(4-(dimethylamino)phenyl)phthalide (I: $X=(CH_3CH_2)_2N$, $Y^2=Z^4=Z^5=Z^6=Z^7=H$, $Y^4=CH_3)_2N$) (10.92 g., m.p. 117°–119° C.).

EXAMPLE 17

A mixture of 2-(4-diethylamino)benzoyl)benzoic acid (5.94 g.), N,N,N',N'-tetraethyl-m-phenylenediamine (4.84 g.) and acetic anhydride (3 ml.) was heated at 70° C. Addition of methanol (20 ml.) afforded 3-(2,4-bis(diethylamino)phenyl)-3-(4-(diethylamino)phenyl)phthalide (I: $X=Y^4=(CH_3CH_2)_2N$, $Y^2=Z^4=Z^5=Z^6=Z^7=H$) (7.1 g., 135°–137° C.).

EXAMPLE 18

A mixture of 2-(2-methyl-4-(diethylamino)benzoyl)benzoic acid (12.48 g.), N,N,N',N'-tetraethyl-m-phenylenediamine (10.56 g.) and acetic anhydride (12 ml.) was warmed (at 40°±8° C.) during one hour, diluted with water (50 ml.,) then 100 ml.), adjusted to pH 4.6 and filtered. The filtrate was clarified with water and adjusted to pH 5.5. Recrystallization of the resulting product (m.p. 134°–140° C.) from methanol afforded 3-(2,4-bis(diethylamino)phenyl)-3-(2-methyl-4-(diethylamino)phenyl)phthalide (I: $X=Y^4=(CH_3CH_2)_2N$, $Y^2=CH_3$, $Z^4=Z^5=Z^6=Z^7=H$) (m.p. 149°–151° C.).

EXAMPLE 19

A. A mixture of tetrachlorophthalic anhydride (42.8 g.), N,N-dimethylaniline (61 g.), aluminum chloride (60 g.) and chlorobenzene (180 ml.) was heated (to 75° C.) during one and one-half hours, then diluted with ice-water (500 ml.). The chlorobenzene layer was separated and steam distilled. The residue was heated (to 95° C.) with dilute sulfuric acid (50%, 250 ml.) and cooled, affording 2-(4-(dimethylamino)benzoyl)-3,4,5,6-tetrachlorobenzoic acid (IV: $Y^2=H$, $Y'^4=(CH_3)_2$, $Z^4=Z''^5=Z''^6=Z^7=Cl$) (57.4 g., m.p. 216°–217° C.).

B. A mixture of 2-(4-(dimethylamino)benzoyl)-3,4,5,6-tetrachlorobenzoic acid (20.3 g.), N,N,N',N'-tetramethyl-m-phenylenediamine (88%, 9.3 g.) and acetic anhydride (74 ml.) was heated (to 95° C.) during one hour, then cooled, affording 3-(2,4-bis(dimethylamino)phenyl)-3-(4-(dimethylamino)phenyl)-4,5,6,7-tetrachlorophthalide (I: $X=Y^4=(CH_3)_2N$, $Y^2=H$, $Z^4=Z^5=Z^6=Z^7=Cl$) (20.3 g., m.p. 227°–229° C.).

EXAMPLE 20

A. A mixture of tetrachlorophthalic anhydride (42.8 g.), N,N-diethylaniline (74 g.), aluminum chloride (60 g.) and chlorobenzene (180 ml.) was heated (to 75° C.) during one and one-half hours, then diluted with ice-water (500 ml.). The chlorobenzene layer was separated and steam distilled. Addition of sodium hydroxide solution (50%) to a solution of the residue in dilute sulfuric acid (50%, 250 ml.) afforded 2-(4-(diethylamino)benzoyl)-3,4,5,6-tetrachlorobenzoic acid (IV: $Y^2=H$, $Y'^4=(CH_3CH_2)_2N$, $Z^4=Z''^5=Z''^6=Z^7=Cl$) (59 g., m.p. 228°–233° C.).

B. A mixture of 2-(4-(diethylamino)benzoyl)-3,4,5,6-tetrachlorobenzoic acid (8.70 g.), N,N,N',N'-tetramethyl-m-phenylenediamine (3.61 g.) and acetic anhydride (5 ml.) was heated (to 90° C.). Addition of methanol (10 ml.) and slurrying the resulting product with methanol afforded 3-(2,4-bis(dimethylamino)phenyl)-3-(4-(diethylamino)phenyl)-4,5,6,7-tetrachlorophthalide (I: $X=(CH_3)_2N$, $Y^2=H$, $Y^4=(CH_3CH_2)_2N$, $Z^4=Z^5=Z^6=Z^7=Cl$) (5.60 g., m.p. 206°–207.5° C.).

EXAMPLE 21

A mixture of 2-(4-(dimethylamino)benzoyl)-3,4,5,6-tetrachlorobenzoic acid (16.28 g.), N,N,N',N'-tetraethyl-m-phenylenediamine (9.68 g.) and acetic anhydride (10 ml.) was heated (at 91° C.) during two hours. Addition of methanol (20 ml., then 12 ml., then 10 ml.) afforded 3-(2,4-bis(diethylamino)phenyl)-3-(4-(dimethylamino)phenyl)-4,5,6,7-tetrachlorophthalide (I: $X=(CH_3CH_2)_2N$, $Y^2=H$, $Y^4=(CH_3)_2N$, $Z^4=Z^5=Z^6=Z^7=Cl$) in three fractions (m.p. 174°–176° C., m.p. 180°–181° C. and m.p. 180°–181° C.).

EXAMPLE 22

A mixture of 2-(4-(diethylamino)benzoyl)-3,4,5,6-tetrachlorobenzoic acid (8.70 g.) N,N,N',N'-tetraethyl-m-phenylenediamine (4.85 g.) and acetic anhydride (5 ml.) was heated (to 90° C.). Addition of methanol (10 ml.) and slurrying the resulting product with methanol (20 ml.) afforded 3-(2,4-bis(diethylamino)phenyl)-3-(4-(diethylamino)phenyl)-4,5,6,7-tetrachlorophthalide (I: $X=Y^4=(CH_3CH_2)_2N$, $Y^2=H$, $Z^4=Z^5=Z^6=Z^7=Cl$) (7.85 g., m.p. 196°–197° C.).

EXAMPLE 23

A mixture of 2-(2-methyl-4-(diethylamino)benzoyl)-3,4,5,6-tetrachlorobenzoic acid (44.9 g.), N,N,N',N'-tetraethyl-m-phenylenediamine (29.7 g.) and acetic anhydride (50 ml.) was heated (at 85°–90° C.) during three hours. The resulting crystalline product was washed with methanol, slurried in hot ethanol and washed again with methanol, affording 3-(2,4-bis(diethylamino)phenyl)-3-(2-methyl-4-(diethylamino)phenyl)-4,5,6,7-tetrachloropthalide (I: $X=Y^4=(CH_3CH_2)_2N$, $Y^2=CH_3$, $Z^4=Z^5=Z^6=Z^7=Cl$) (34.1 g., m.p. 162°–164° C.).

EXAMPLE 24

A. A mixture of phthalic anhydride (11.2 g.), N,N-diethyl-m-chloroaniline (28.2 g.), aluminum chloride (30 g.) and chlorobenzene (75 ml.) was heated (to 90° C.), then diluted with water (300 ml.). The chlorobenzene layer was separated and steam distilled. Adjustment of the pH of the aqueous residue to about 3 afforded 2-(2-chloro-4-(diethylamino)benzoyl)benzoic acid (II: $Y'^2=Cl$, $Y'^4=(CH_3CH_2)_2N$, $Z^4=Z'^5=Z'^6=Z^7=H$) (15.9 g., m.p. 140°–144° C.).

B. A mixture of 2-(2-chloro-4-(diethylamino)benzoyl)benzoic acid (6.61 g.), N,N,N',N'-tetraethyl-m-phenylenediamine (4.30 g.) and acetic anhydride (5 ml.) was allowed to stand overnight at room temperature, then diluted with methanol (10 ml.), affording 3-(2,4-bis(diethylamino)phenyl)-3-(2-chloro-4-(diethylamino)phenyl)phthalide (I: $X=Y^4=(CH_3CH_2)_2N$, $Y^2=Cl$, $Z^4=Z^5=Z^6=Z^7=H$) (3.94 g., m.p. 141°–143° C.).

By methods similar to those described in the foregoing examples the following additional 2-benzoylbenzoic acids of Formula IV (Table I) and 3,3-diphenylphthalides of Formula I (Table II) were prepared or can be prepared.

Table I:

2-Benzoylbenzoic Acids

| Example | Y² | Y'⁴ | Z⁴ | Z''⁵ | Z''⁶ | Z⁷ | M.p.(°C.) | % Yield |
|---------|----|----|----|------|------|----|-----------|---------|
| 25A | H | CH₂CH₂OCH₂CH₂N | Cl | Cl | Cl | Cl | 222–225 | 12 |
| 26A | H | CH₂CH₂OCH₂CH₂N | H | H | H | H | 104–107 | 83 |
| 28A | CH₃ | (CH₃CH₂)₂N | — | H₂Cl₂ | — | — | 199–206 | 68 |
| 29A | CH₃ | (CH₃CH₂)₂N | Br | Br | Br | Br | 202–205 | 91 |
| 30A | H | (CH₃CH₂)(C₆H₅CH₂)N | Cl | Cl | Cl | Cl | 116–132 | |
| 32A | CH₃ | (CH₃)₂N | H | H | H | H | 106–110 | 64 |
| 33A | (CH₃CH₂)₂N | (CH₃CH₂)₂N | Cl | Cl | Cl | Cl | 174–178 | |
| 35A | H | (CH₃CH₂)(C₆H₅CH₂)N | H | H | H | H | 197–200 | 39 |
| 36A | H | CH₂(CH₂)₃N | Cl | Cl | Cl | Cl | 100–102 | 69 |
| 37A | CH₃ | CH₂(CH₂)₃N | Cl | Cl | Cl | Cl | 58–66 | 84 |
| 38A | H | CH₂(CH₂)₃N | H | H | H | H | 110–120 | 22 |
| 40A | H | CH₃(4-CH₃OC₆H₄)N | H | H | H | H | 235–242 | 30 |
| 41A | H | CH₃(4-CH₃OC₆H₄)N | Cl | Cl | Cl | Cl | 128–130 | 66 |
| 42A | CH₃ | CH₂(CH₂)₃N | H | H | H | H | 183–187 | 80 |
| 43A | H | CH₂(CH₂)₄N | H | H | H | H | 200 dec. | 71 |
| 45A | (CH₃CH₂)₂N | (CH₃CH₂)₂ | H | H | H | H | 189–190 | 17 |

Table II:

3,3-Diphenylphthalides

| Example | X | Y² | Y⁴ | Z⁴ | Z⁵ | Z⁶ | Z⁷ | M.p.(°C.) | % Yield |
|---------|---|----|----|----|----|----|----|-----------|---------|
| 25B | (CH₃)₂N | H | CH₂CH₂OCH₂CH₂N | Cl | Cl | Cl | Cl | 250–251 | 20 |
| 26B | (CH₃)₂N | H | CH₂CH₂OCH₂CH₂N | H | H | H | H | 208–210 | 64 |
| 27 | (CH₃CH₂)₂N | H | CH₂CH₂OCH₂CH₂N | H | H | H | H | 157–158 | 96 |
| 28B | (CH₃CH₂)₂N | CH₃ | (CH₃CH₂)₂N | — | H₂Cl₂ | — | — | 169–172 | 18 |
| 29B | (CH₃)₂N | CH₃ | (CH₃CH₂)₂N | Br | Br | Br | Br | 245–246 | 51 |
| 30B | (CH₃)₂N | H | (CH₃CH₂)(C₆H₅CH₂)N | Cl | Cl | Cl | Cl | 180–182 | 26 |
| 31 | (CH₃)₂N | H | CH₂(CH₂)₃N | H | H | (CH₃)₂N | H | 128–130 | |
| 32B | (CH₃)₂N | CH₃ | (CH₃)₂N | H | H | H | H | 224–228 | 64 |
| 33B | (CH₃)₂N | (CH₃CH₂)₂N | (CH₃CH₂)₂N | Cl | Cl | Cl | Cl | 132–135 | |
| 34 | (CH₃)₂N | CH₃ | (CH₃CH₂)₂N | — | H₂Cl₂ | — | — | 186–192 | 32 |
| 35B | (CH₃)₂N | H | (CH₃CH₂)8C₆H₅CH₂)N | H | H | H | H | 130–132 | 98 |
| 36B | (CH₃)₂N | H | CH₂(CH₂)₃N | Cl | Cl | Cl | Cl | 276–279 | 43 |
| 37B | (CH₃)₂N | CH₃ | CH₂(CH₂)₃N | Cl | Cl | Cl | Cl | 245–249 | 56 |
| 38B | (CH₃)₂N | H | CH₂(CH₂)₃N | H | H | H | H | 192–194 | 68 |
| 39 | (CH₃CH₂)₂N | H | (CH₃)₂N | H | H | (CH₃)₂N | H | 68–72 | 74 |
| 40B | (CH₃)₂N | H | CH₃(4-CH₃OC₆H₄)N | H | H | H | H | 155–158 | |
| 41B | (CH₃)₂N | H | CH₃(4-CH₃OC₆H₄)N | Cl | Cl | Cl | Cl | 254–256 | 21 |
| 42B | (CH₃)₂N | CH₃ | CH₂(CH₂)₃N | H | H | H | H | 244–247 | 59 |
| 43B | (CH₃)₂N | H | CH₂(CH₂)₄N | H | H | H | H | 192–194 | 63 |
| 44 | CH₂(CH₂)₃N | CH₃ | (CH₃CH₂)₂N | H | H | H | H | 163–165 | 16 |
| 45B | (CH₃CH₂)₂N | (CH₃CH₂)₂N | (CH₃CH₂)₂N | H | H | H | H | 149–151 | 33 |
| 46 | (CH₃CH₂)₂N | H | (CH₃CH₂)(C₆H₅CH₂)N | Cl | Cl | Cl | Cl | 139–142 | 39 |
| 47 | (CH₃Ch₂)₂)₂N | (CH₃CH₂)₂N | (CH₃CH₂)₂N | Cl | Cl | Cl | Cl | 110–117 | 27 |

Table II:-continued

| Example | X | $Y^2$ | 3,3-Diphenylphthalides $Y^4$ | $Z^4$ | $Z^5$ | $Z^6$ | $Z^7$ | M.p.(°C.) | % Yield |
|---|---|---|---|---|---|---|---|---|---|
| 48 | CH$_2$(CH$_2$)$_3$N | CH$_3$ | (CH$_3$CH$_2$)$_2$N | Cl | Cl | Cl | Cl | 135–137 | 84 |

EXAMPLE 49

3-(2,4-Bis(dimethylamino)phenyl)-3-(2-methyl-4-(diethylamino)phenyl)phthalide (Example 2B) and 3-(2,4-bis(dimethylamino)phenyl)-3-(4-(dimethylamino)phenyl)-6-(dimethylamino)phthalide (Example 12C) were microencapsulated as follows. A solution of the color precursor (1.46 g.) in isopropylbisphenyl (60 g.) and a solution of carboxymethylcellulose (5 g.) in water (200 ml.) were mixed and emulsified by rapid stirring. The desired particle size (5 microns) was checked by microscope. To the emulsion was added a solution of pigskin gelatin (15 g.) in water (120 ml.). The pH was adjusted to 6.5 with aqueous sodium hydroxide (10%) with rapid stirring. Water (670 ml.) was added slowly with heating (at 50° C.). The pH was adjusted to 4.5 with aqueous acetic acid (10%) with continued rapid stirring (5 min.). Aqueous glutaraldehyde (10 g., 25%) was added with continued rapid stirring (15 min.).

The microcapsule mixture was stirred more slowly overnight, diluted with water (to 1120 g.), and coated onto white typewriter paper sheets (0.0015 in. film thickness). The sheets were air dried. Duplicate typewritten images were made on four types of receiving sheets, three coated with phenolic resins and one coated with acid clay. The color precursor of Example 2B produced blue-black images on the receiving sheets coated with phenolic resins and a brown image on the receiving sheets coated with acidic clay. The color precursor of Example 12C produced deep purple images on the receiving sheets coated with phenolic resins and a blue-black image on the receiving sheet coated with acidic clay.

EXAMPLE 50

Polyvinyl alcohol dispersions of the color precursors of Example 2B (2.0 g.) and Example 12C (2.0 g.) were prepared by shaking with water (3.7 g.), aqueous polyvinyl alcohol (10%, 8.6 g.) and zirconium grinding beads (10 g.). A polyvinyl alcohol dispersion of bisphenol A (9.8 g.) was prepared by shaking with water (18.2 g.), aqueous polyvinyl alcohol (10%, 42 g.) and zirconium grinding beads (70 ml.). A mixture of each of the color precursor dispersions (2.1 g. of each) and the bisphenol A dispersion (47.9 g.) was made by thorough mixing. Each mixture was coated (at thicknesses of 0.003 in. and 0.0015 in.) onto white mimeo paper sheets and the sheets were dried at room temperature. Contacting the coated sheets with a heated stylus (150° C.) produced a blue-black image on the sheet coated with the color precursor of Example 2B and a deep purple image on the sheet coated with the color precursor of Example 12C.

We claim:

1. 3-(2-X-4-X-Phenyl)-3-(2-$Y^2$-4-phenyl)-4-$Z^4$-5-$Z^5$-6-$Z^6$-7-$Z^7$-phthalide wherein:
   X is dialkylamino wherein alkyl is non-tertiary alkyl of one to four carbon atoms;
   $Y^2$ is hydrogen, non-tertiary alkyl of one to four carbon atoms, alkanoylamino of two to five carbon atoms, non-tertiary alkoxy of one to four carbon atoms or halo;
   $Y^4$ is morpholino;
   $Z^4$ is hydrogen or halo;
   $Z^5$ is hydrogen or halo; or non-tertiary alkyl of one to four carbon atoms, nitro, amino or dialkylamino wherein alkyl is non-tertiary alkyl of one to four carbon atoms when $Z^4$, $Z^6$ and $Z^7$ are each hydrogen;
   $Z^6$ is hydrogen or halo; or non-tertiary alkyl of one to four carbon atoms, nitro, amino or dialkylamino wherein alkyl is non-tertiary alkyl of one to four carbon atoms when $Z^4$, $Z^5$ and $Z^7$ are each hydrogen; and
   $Z^7$ is hydrogen or halo.

2. A compound according to claim 1 wherein $Z^4$, $Z^5$, $Z^6$ and $Z^7$ are each hydrogen.

3. A compound according to claim 2 wherein $Y^2$ is hydrogen.

4. A compound according to claim 3 wherein X is dimethylamino.

* * * * *